(12) United States Patent
Bozzoni et al.

(10) Patent No.: US 9,034,838 B2
(45) Date of Patent: May 19, 2015

(54) MIR-31 IN DUCHENNE MUSCULAR DYSTROPHY THERAPY

(75) Inventors: Irene Bozzoni, Rome (IT); Julie Martone, Rome (IT); Davide Cacchiarelli, Rome (IT); Tania Incitti, Rome (IT)

(73) Assignee: UNIVERSITA DEGLI STUDI DI ROMA "LA SAPIENZA", Rome (IT)

( * ) Notice: Subject to any disclaimer, the term of this patent is extended or adjusted under 35 U.S.C. 154(b) by 130 days.

(21) Appl. No.: 13/322,023

(22) PCT Filed: May 24, 2010

(86) PCT No.: PCT/EP2010/057093
§ 371 (c)(1),
(2), (4) Date: Jan. 24, 2012

(87) PCT Pub. No.: WO2010/136417
PCT Pub. Date: Dec. 2, 2010

(65) Prior Publication Data
US 2012/0129920 A1 May 24, 2012

(30) Foreign Application Priority Data

May 25, 2009 (EP) .................................... 09161038

(51) Int. Cl.
*C12Q 1/68* (2006.01)
*C12N 15/113* (2010.01)

(52) U.S. Cl.
CPC ............ *C12Q 1/6883* (2013.01); *C12N 15/113* (2013.01); *C12N 2310/113* (2013.01); *C12N 2310/3231* (2013.01); *C12Q 2600/158* (2013.01); *C12Q 2600/178* (2013.01)

(58) Field of Classification Search
USPC ............... 435/6, 6.1, 91.1, 91.31, 320.1, 455; 514/44; 536/23.1, 24.5, 24.1
See application file for complete search history.

(56) References Cited

U.S. PATENT DOCUMENTS

2005/0255487 A1 * 11/2005 Khvorova et al. ................ 435/6

FOREIGN PATENT DOCUMENTS

| JP | 2010/510964 | * | 4/2010 |
| WO | 2006/137941 A2 | | 12/2006 |
| WO | 2008/142567 A2 | | 11/2008 |

OTHER PUBLICATIONS

Sequence Alignment data.*
Eisenberg, Iris, et al.: "Distinctive patterns of microRNA expression in primary muscular disorders", Proceedings of the National Academy of Sciences of the United States (PNAS), National Academy of Science, US LNKD-DOI: 10.1073/PNAS.0708115104, vol. 104, No. 43, Oct. 1, 2007, pp. 17016-17021, XP002532416, ISSN : 0027-8424, the whole document.
Callis, Thomas, E., et al.: "Muscling through the microRNA world". Experimental Biology and Medicine, Society for Experimental Biology and Medicine, US LNKD-DOI: 10.3181/0709-MR-237, vol. 233, No. 2, Feb. 1, 2008, pp. 131-138, XP002532418, ISSN: 1535-3702, the whole document.
Greco, Simona, et al.: "Common micro-RNA signature in skeletal muscle damage and regeneration induced by Duchenne muscular dystrophy and acute ischemia", FASEB Journal, vol. 23 , No. 10, Oct. 2009, pp. 3335-3346, XP002S94658, ISSN : 0892-6638, the whole document.

* cited by examiner

*Primary Examiner* — Jane Zara
(74) *Attorney, Agent, or Firm* — Lucas & Mercanti, LLP (57) ABSTRACT

The invention relates to the therapy of Duchenne Muscular Dystrophy (DMD) by means of modulating the amount of a specific miRNA (miR-31).

23 Claims, 5 Drawing Sheets

Fig. 5

SEQUENCE LISTING

```
<160> NUMBER OF SEQ ID NOS: 6

<210> SEQ ID NO 1
<211> LENGTH: 15
<212> TYPE: RNA
<213> ORGANISM: Homo sapiens

<400> SEQUENCE: 1
gaaauggcaa guuau                                                      15

<210> SEQ ID NO 2
<211> LENGTH: 23
<212> TYPE: RNA
<213> ORGANISM: Homo sapiens

<400> SEQUENCE: 2
ccauauaaag aaauggcaag uua                                             23

<210> SEQ ID NO 3
<211> LENGTH: 21
<212> TYPE: RNA
<213> ORGANISM: Homo sapiens

<400> SEQUENCE: 3
aggcaagaug cuggcauagc u                                               21
```

```
<210> SEQ ID NO 4
<211> LENGTH: 106
<212> TYPE: RNA
<213> ORGANISM: Homo sapiens

<400> SEQUENCE: 4
ggcagcuaug uuugcaucuu gccucacaca gcuauguuug caucuugccu cacacagcua      60
uguuugcauc uugccucaca cagcuauguu ugcaucuugc cuccgc                   106

<210> SEQ ID NO 5
<211> LENGTH: 106
<212> TYPE: DNA
<213> ORGANISM: Homo sapiens

<400> SEQUENCE: 5
ggcagctatg tttgcatctt gcctcacaca gctatgtttg catcttgcct cacacagcta     60
tgtttgcatc ttgcctcaca cagctatgtt tgcatcttgc ctccgc                   106

<210> SEQ ID NO 6
<211> LENGTH: 35
<212> TYPE: RNA
<213> ORGANISM: Homo sapiens

<400> SEQUENCE: 6
uugauagcua aauaacuugc cauuucuuua uaugg                                35
```

MIR-31 IN DUCHENNE MUSCULAR DYSTROPHY THERAPY

CROSS-REFERENCE TO RELATED APPLICATIONS

This application is a 371 of PCT/EP2010/057093, filed on May 24, 2010, which claims the benefit of European Patent Application No. 09161038.6, filed on May 25, 2009, the contents of each of which are incorporated herein by reference.

FIELD OF THE INVENTION

The invention relates to the therapy of Duchenne Muscular Dystrophy (DMD) by means of modulating the amount of a specific miRNA.

BACKGROUND

In Duchenne Muscular Dystrophy, the absence of dystrophin leads to a dramatic decrease of the Dystrophin-Associated Protein Complex (DAPC) required to connect intracellular actin microfilaments to the extracellular matrix (Matsumura et al., 1994; Ervasti et al., 2008). As a consequence, the muscle fibers become more sensitive to mechanical damage leading to muscle degeneration, chronic inflammatory response and increase in fibrosis, all of which exacerbate the dystrophic phenotype. As a consequence, alterations of many cellular processes occur. At present, several therapeutic strategies have been successfully tested in animal models of muscular dystrophies and some of them are currently entering clinical trials. Among the most promising approaches, exon skipping allows the rescue of dystrophin synthesis through the production of a shorter but functional mRNA (Denti et al., 2006, 2008).

The authors identify a miRNA (miR-31), particularly abundant in dystrophic regenerating fibers that represses dystrophin expression. They also show that by means of sequestering miR-31 or of protecting its target sequence on the dystrophin 3'UTR, an increase of translation of dystrophin is obtained.

DESCRIPTION OF THE INVENTION miRNAs are molecules known to play crucial functions in the differentiation commitment of several cell types and to be involved in many pathological processes. In this work, the authors identified a specific signature of miRNAs that is correlated with the DMD pathology. They found a different miRNA expression profile between wild type and Duchenne conditions. A specific miRNA, miR-31, was found at higher levels in mdx as well as in human DMD muscles with respect to wild type conditions. As a matter of fact, miR-31 increases by 30-50 fold in mouse dystrophic muscles and 7-10 fold in human DMD biopsies. The authors observed that, in murine and human myoblasts, the abundance of miR-31 was inversely correlated with the amount of dystrophin. Experiments of overexpression and depletion, both in vitro and in vivo, together with classical luciferase assays validated the dystrophin mRNA as a target of miR-31, allowing the authors to conclude that dystrophin is negatively controlled at the translation level by miR-31. The authors further demonstrated that in human DMD myoblasts cured through the exon skipping approach, sponge-mediated depletion of miR-31 increased the efficiency of dystrophin rescue. In vivo data were also provided on the efficacy of miR-31 depletion on dystrophin translation: local injection of a miR-31 derivative, namely an "oligo protector" complementary to the miR-31 target sequence on the dystrophin mRNA strongly improved its translation in mdx mice treated with the exon skipping approach. These results indicated that depleting miR-31 in muscle cells or inhibiting its activity on the dystrophin mRNA can provide a further improvement to those DMD therapies in which one wants to efficiently recover dystrophin synthesis.

miR-31 is expressed in regenerating fibers which are activated in Duchenne conditions. Since it targets dystrophin mRNA and represses its translation, its depletion can increase dystrophin translation with potential therapeutic benefits in all those cases where DMD therapeutic strategies are based on the recovery of dystrophin expression (i.e. exon skipping).

The authors found that specific nucleic acid molecules act as a "sponge" for miR-31. In particular they constructed a molecule having a RNA sequence containing multiple target sites for miR-31. When expressed in cells, such molecules are able to sequester endogenous miR-31 and to prevent its repression activity on dystrophin mRNA, thus allowing its efficient translation. Preferentially, the sequence of such molecules is included in the 3'UTR of a carrier mRNA and is specifically expressed under the control of a muscle-specific promoter.

Moreover the authors found that other specific nucleic acid molecules act as "protectors" of dystrophin mRNA against miR-31 repression, achieving the same result of functional inactivation of the action of the miR-31 miRNA on the dystrophin RNA.

In particular they constructed nucleic acid molecules comprising a region complementary to the 3'UTR dystrophin mRNA region which is recognized by the miR-31 sequence (5'-GGCAAG-3'). By competing for miR-31 binding, such molecules are able to prevent the translational repression mediated by miR-31. The molecule is provided as a synthetic oligo or as part of a chimeric RNA in a gene therapy approach. The protector sequence, i.e. for efficient uptake in vivo, would preferably have the length of approximately 15 nucleotides (5'-GAAAUGGCAAGUUAU-3'; SEQ ID No. 1), while, i.e. for in vitro transfection, could be longer up to appr. 30 nucleotides, as for example, the 23 oligonucleotide 5'-CCAUAUAAAGAAAUGGCAAGUUA-3'; SEQ ID No. 2. The region corresponding to the miR-31 sequence recognizing the dystrophin 3'UTR is underlined.

Therefore it is an object of the invention a nucleic acid molecule or a derivative thereof able to functional inactivate the action of the miR-31 miRNA on the dystrophin RNA (NCBI accession ID: NM_004006). A "derivative" is a nucleic acid molecule, as a DNA molecule, coding the nucleic acid molecule of the invention, or a nucleic acid molecule comprising the nucleotide sequence of the nucleic acid molecule of the invention.

In a first preferred embodiment of the invention, the molecule is able to bind to the miR-31 by sequence complementarity and consequently selectively sequester the miR-31 in muscle cells. In order to sequester the miRNA more efficiently, the sequence preferably comprises more than one sequence, each one being complementary to the miR-31 sequence: 5'-aggcaagaugcuggcauagcu-3' (SEQ ID No. 3). However, in order not to get the cleavage of the substrate (the miRNA), a non perfect match is preferred (Rivas F V et al. 2005); therefore at least one nucleotide of the nucleic acid molecule of the invention is not complementary to the corresponding nucleotide comprised in the region from nt. 9 to nt. 14 of the miR-31 sequence. In a preferred embodiment at least three nucleotides of the nucleic acid molecule of the invention are not complementary to the corresponding nucleotides comprised in the region from nt. 9 to nt. 14 of the miR-31 sequence.

In a particularly preferred embodiment the nucleic acid molecule essentially consists of a molecule having the following sequence:

(SEQ ID No. 4)
5'ggcagcuauguuugcaucuugccucacacagcuauguuugcaucuug ccucacacagcuauguuugcaucuugccucacacagcuauguuugcauc uugccuccgc-3'.

The nucleic acid molecule or a derivative thereof as above disclosed may be advantageously comprised in the 3'UTR of a transcript whose expression is driven by a muscle-specific promoter.

It is another object of the invention an expression vector for gene therapy comprising a sequence encoding the nucleic acid molecule fused to the a muscle-specific promoter. A muscle-specific promoter is a promoter driving selectively the transcription of an operatively linked sequence in muscle cell lineages. The expression vector for gene therapy is preferentially an AAV (Adeno-associated viruses) vector comprising a muscle-specific promoter. Preferably the muscle-specific promoter is active in early phases of muscle differentiation. The expression vector for gene therapy is advantageously produced as AAV viral particle which preferentially transduces muscle cells. The combination of these two features, namely the muscle specificity of the promoter and the selectivity for muscle cells of the viral particle, ensures the restricted expression of the nucleic acid molecule of the invention in muscle cells.

In a further preferred embodiment of the invention the molecule is able to compete with the miR-31 molecule for the binding to the 3'UTR dystrophin mRNA. Preferably the molecule comprises a sequence that is complementary to the 3'UTR dystrophin mRNA region which is recognized by the miR-31 sequence 5'-GGCAAG-3'. More preferably the nucleic acid molecule comprises a sequence that is complementary to the 3'UTR dystrophin mRNA region, said region comprising the sequence: 5'-CUUGCC-3'. More preferably the nucleic acid molecule is an oligonucleotide of appr. 15 nucleotides fully complementary to the 3'UTR dystrophin mRNA region comprising the sequence: 5'-CUUGCC-3'; most preferably the nucleic acid molecule comprises the sequence 5'-GAAAUGGCAAGUUAU-3' (SEQ ID No. 1). In an aspect the nucleic acid molecule is a modified synthetic oligonucleotide, preferably belonging to the group of: LNA (Locked Nucleic Acid), methylated oligos, phosphoro-thiolated oligos.

The nucleic acid molecules of the invention as above disclosed that are able to functional inactivate the action of the miR-31 miRNA on the dystrophin RNA are also provided as an expression vector for gene therapy comprising a sequence encoding the nucleic acid molecule fused to the a muscle-specific promoter. A muscle-specific promoter is a promoter driving selectively the transcription of an operatively linked sequence in muscle cell lineages. The expression vector for gene therapy is preferentially an AAV vector comprising a muscle-specific promoter. Preferably the muscle-specific promoter is active in early phases of muscle differentiation. The expression vector for gene therapy is advantageously produced as AAV viral particle which preferentially transduces muscle cells. The combination of these two features, namely the muscle specificity of the promoter and the selectivity for muscle cells of the viral particle, ensures the restricted expression of the nucleic acid molecule of the invention in muscle cells.

It is a further object of the invention to provide the nucleic acid molecule as above disclosed for medical use, in particular for medical use for muscle degenerative disorders, as Muscular Dystrophies, particularly Duchenne Muscular Dystrophy. The nucleic acid molecule disclosed herein may be advantageously used for increasing the translation of dystrophin in a host in need thereof, by administering to the host a therapeutically active amount of the said nucleic acid molecule.

A particular aspect is to improve the so-called exon-skipping therapeutic approach or other strategies where one wants to increase the efficiency of dystrophin translation in the treatment of Duchenne Muscular Dystrophy, to recover a correct dystrophin expression by administering the nucleic acid molecule of the invention, either directly or by means of gene therapy.

FIGURE LEGENDS

FIG. 1. miR-31 expression. (A) miR-31 relative expression in WT and mdx mice, measured by qRT-PCR. (B) In situ hybridization of miR-31 in mdx gastrocnemius. (C) miR-31 relative expression in WT (black bars) and mdx (grey bars) mouse satellite cells, measured by qRT-PCR in growth medium (/) and at the indicated time points after shift to differentiation medium. (D) The same cells were analyzed by Western blot for dystrophin and actinin proteins. (E) qRT-PCR of miR-31 relative expression in human muscle biopsies from healthy (Ctrl), Duchenne (DMD) and Becker (BMD) donors. (F) qRT-PCR of miR-31 relative expression in human primary myoblasts from healthy donors (Ctrl, black bars) or DMD patients (DMD, grey bars) in growth medium (/) and at the indicated time points after shift to differentiation medium. (G) The same cells were analyzed by Western blot for Pax7, MHC, dystrophin and actinin proteins.

FIG. 2. miR-31 and dystrophin expression in mouse myoblasts. (A) Northern and Western blot analysis on RNA (miR-31) and proteins (Dystrophin and actinin) from C2 mouse myoblasts in growth medium (GM) and at 3 and 5 days in differentiation medium (DM). (B) Representative Western blots with anti-dystrophin and anti-actinin antibodies in C2 myoblasts infected with a mock lentivirus (ctrl) or with one carrying a miR-31 expression cassette (LmiR-31) at 3 and 5 days of differentiation. In all the experiments the dystrophin levels were measured from three independent experiments and normalized to actinin expression (histograms at the bottom). miR-31 expression levels (panels miR-31) were measured by Northern blot. (C) As in panel B) with the difference that C2 myoblasts were transfected with an anti-miR-31 (LNA-31) or scrambled LNA oligos and incubated 3 days in differentiation medium.

FIG. 5. Inhibition of miR-31 activity enhances dystrophin rescue upon exon skipping. (A) Schematic representation of the exon skipping strategy in the human DMD D48-50 deletion. (B) D48-50 myoblasts were infected with a lentiviral construct expressing the antisense molecules able to induce exon skipping (U1#51), alone (Ctrl) or together with a lentivirus expressing the sponge construct (miR-31s). Mock are uninfected D48-50 myoblasts. RQ (Relative Quantification) levels were calculated with respect to the actinin control from three independent experiments. (C) D48-50 myoblasts were infected with the U1#51 lentivirus alone (Ctrl) or together with a miR-31 expression cassette (Lmir-31). Mock are uninfected D48-50 myoblasts. RQ (Relative Quantification) levels were calculated with respect to the actinin control from three independent experiments. (D) Schematic representation of the exon skipping strategy in the mdx mouse. (E) AAV viruses, expressing exon 23-antisense RNAs (AAV-U1#23, FIG. 5D), were injected into tibialis muscles. After one week, miR-31 target protector LNA oligos were locally injected in the right tibialis (+), while control scrambled oligos were administered in the contro-lateral leg (−). After an additional week, muscles were dissected and proteins analyzed. The diagram shows the average values of dystrophin accumulation from three independent experiments.

MATERIALS AND METHODS

Sequence of miRNAs Under Analysis

Mature miRNAs as below show perfect sequence conservation between human and mouse. The mature sequence of the human miRNA miR-31 is:

5' <u>aggcaag</u>augcuggcauagcu 3' (SEQ ID No. 3; Sanger ID No. MIMAT0000089, http://www.mirbase.org/); the underlined nucleotides refer to a sequence complementary to the 5'-CUUGCC-3' sequence on the 3'UTR of the Dystrophin RNA.

3' UTR sequence of the miR-31 Sponge construct, cloned in SACII sites of the lentiviral vector pRRLSIN.cPPT.PGK/GFP.WPRE (Bonci et al., 2003):

```
                                              (SEQ ID No. 5)
5'-ggcagctatgtttgcatcttgcctcacacagctatgtttgcatctt gcctcacacagctatgtttgcatcttgcctcacacagctatgtttgcat cttgcctccgc-3'.
```

The underlined sequences correspond to miR-31 binding sites with non-perfect complementarity in the central part (ttt). The non perfect complementarity prevents miR-31 from acting as a siRNA in degrading its substrate.

Examples of protector oligos are:

```
                                              (SEQ ID No. 1)
           5'-GAAAUGGCAAGUUAU-3';

(SEQ ID No. 2)
        5'-CCAUAUAAAGAAAUGGCAAGUUA-3'.
```

The underlined sequence refers to nucleotides complementary to the 5'-CUUGCC-3' sequence on the 3'UTR of the Dystrophin RNA; the protector is able to compete for the binding of miR-31 to the same.

The relation among miR-31, Dystrophin 3'UTR and Protector is as depicted in Table 1.

TABLE 1

| | SEED SEQUENCE |
|---|---|
| miR-31 (SEQ ID No. 3) | 3'UCGAUACGGUCGUA<u>GAACGGA</u> 5' |
| Dystrophin 3'UTR (SEQ ID No. 6) | 5'UUGAUAGCUAAAUAA<u>CUUGCC</u>AUUUCUU UAUAUGG 3' |
| Protector (SEQ ID No. 1) | 3'-UAUU<u>GAACGG</u>UAAAG-5' |

RNA Preparation and Analysis.

Total RNA was prepared from liquid nitrogen powdered tissue homogenized in TRIzol reagent (Invitrogen). miRNAs analysis was performed using specific TaqMan microRNA assays (Applied Biosystems). Relative quantification was performed using sno55 as endogenous control for murine samples and U6 for human samples. Data were expressed as means±SEM, unless otherwise stated. Statistical significance of the differences between means was assessed by t-test (non-parametric). A probability of <5% was considered significant.

Protein and miRNA In Situ Analyses.

Western blots on total protein extracts were performed as described [Denti et al., 2006]. miRNA in situ hybridization was performed in formaldehyde and EDC-fixed tissues according to Pena et al. (2009).

Luciferase Assay.

C2 myoblasts were collected using 250 μL of Passive Lysis Buffer and the assay was performed according to Dual-Luciferase Reporter Assay System protocol (Promega).

Results

Muscle homeostasis depends on the concerted action of molecular mechanisms controlling myogenic proliferation, differentiation and maturation. Modulation of such processes occurs through the combined activity of transcriptional factors and miRNAs which control the expression of a complex network of target genes.

In muscle degenerative disorders, such as Duchenne Muscular Dystrophy (DMD), muscle fiber breakage and degeneration is accompanied by a complex series of events including inflammatory infiltration, intense fibrosis and, most importantly, the activation of satellite cells which provide supply for new tissue formation. The microRNA-mediated control of gene expression appears to be especially important in muscle differentiation (Naguibneva et al., 2006; Chen et al., 2006) and in muscle degenerative diseases where their expression was described to be strongly deregulated (Eisenberg et al., 2007).

Figure 1:
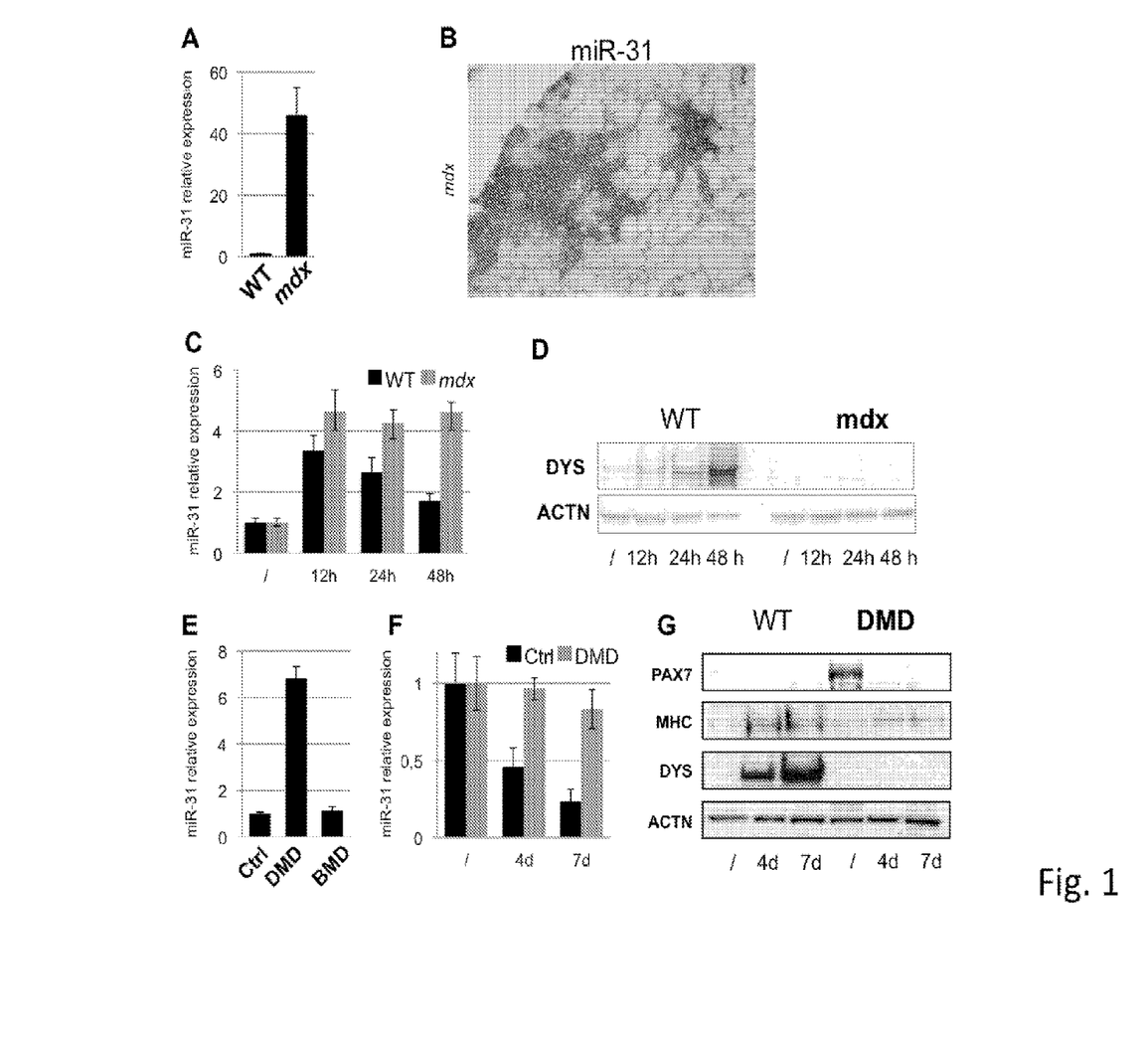

Profile analysis in Duchenne versus wild type muscles indicated that several classes of miRNAs are differentially expressed in mdx mice (Greco et al., 2009). Among these, we found that in a two-month old mdx muscle, miR-31 displays a 40-fold enrichment with respect to control muscles (FIG. 1A). Due to such conspicuous abundance and in consideration of the fact that dystrophic muscles undergo intense tissue reorganization with massive degeneration and regeneration, we tested miR-31 localization by in situ hybridization. FIG. 1B shows that miR-31 has a preferential localization in activated/differentiating satellite cells recognized by the characteristic phenotype of mononucleated fibers, highly abundant in mdx conditions. In line with this, miR-31 localization overlapped with that of miR-206 described to have such a cell specificity (Yuasa et al., 2008). In vitro differentiation of wild type mouse satellite cells indicated that miR-31 is highly expressed when these cells are induced to differentiate and that its expression progressively decreases at later stages of differentiation; on the contrary, in mdx-derived satellite cells the levels of miR-31 remain high even at prolonged differentiation times (FIG. 1C).

miR-31 was observed to be highly abundant also in human DMD biopsies when compared to wild type and Becker muscles (FIG. 1E). Notably, in primary human myoblasts induced to differentiate in vitro, miR-31 levels decreased with progression of differentiation, while, in DMD myoblasts miR-31 accumulation remained high (FIG. 1F). DMD myoblasts appear to have increased regenerative and lower differentiation potential than control cells as shown by the expression of the Pax7 regenerative factor (Buckingham and Relaix, 2007) in growth conditions and by the delayed appearance of the myosin heavy chain (MHC) protein after shift to differentiation conditions (FIG. 1G). The Pax7 detection in primary DMD myoblasts is likely to be due to the fact that, similarly to mdx muscles, DMD biopsies include a relevant proportion of activated satellite cells as expected in a dystrophic muscle.

Altogether, these data indicate that the high levels of miR-31 expression in Duchenne muscles are due on one side to intensive regeneration involving activated satellite cells and on the other to the reduced ability of Duchenne myoblasts to complete the differentiation process.

Figure 2:
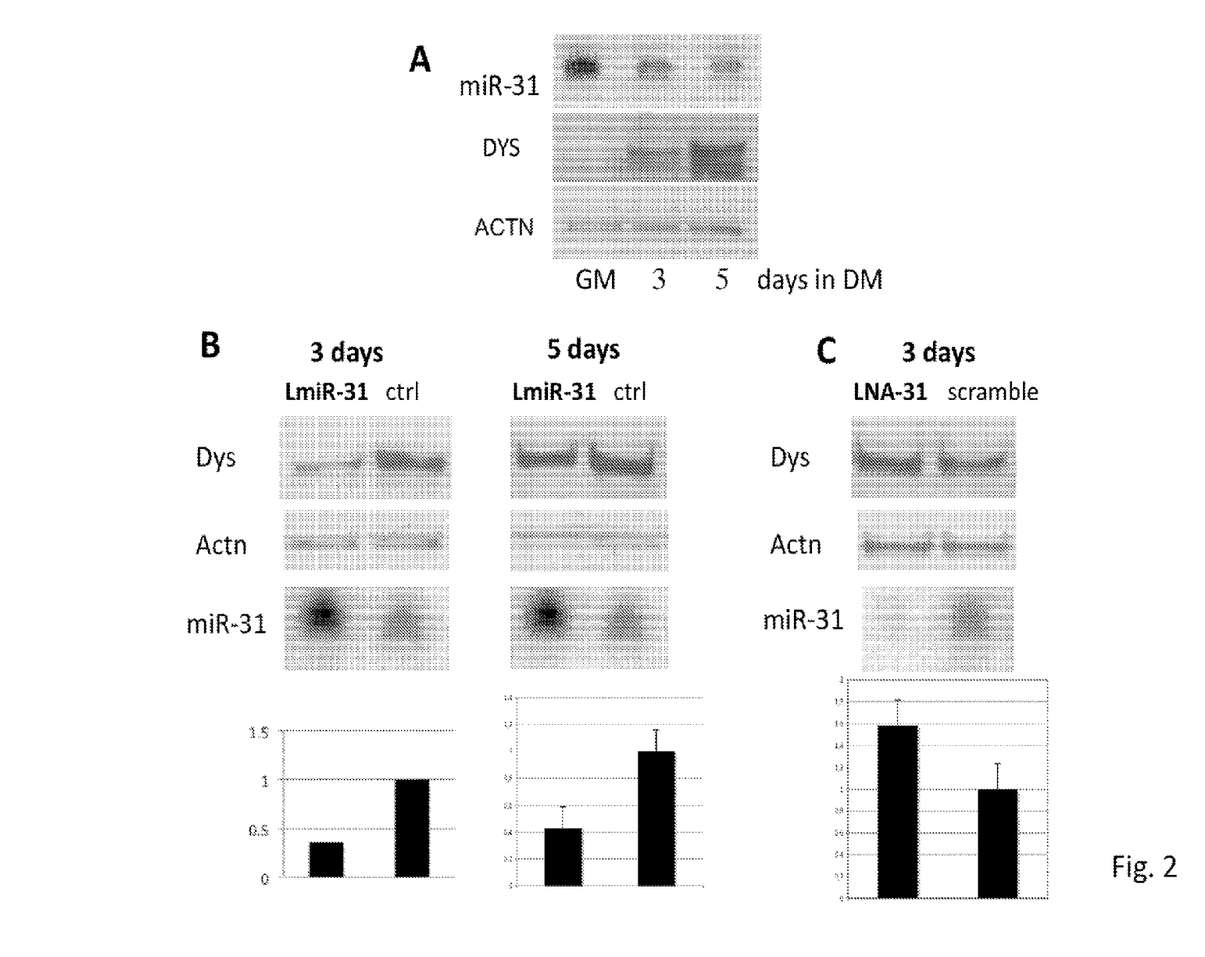

Accumulation of miR-31 was also assessed during in vitro differentiation of C2C12 mouse myoblasts (FIG. 2A, panel miR-31). miR-31 was expressed at fairly good levels in proliferating conditions (GM); however, upon differentiation (days in DM), its levels decreased showing an inverse correlation with the accumulation of dystrophin (FIG. 2A, panel Dys).

Searching for miR-31 targets, we identified one putative binding site in the 3'UTR of the dystrophin mRNA. Both in mouse satellite cultures (FIG. 1C) and in mouse C2 myoblasts differentiated in vitro (FIG. 2A), the decrease in miR-31 accumulation paralleled the increase in dystrophin synthesis, showing the expected inverse correlation between a miRNA and its target. Therefore, we tested whether Dystrophin expression responded to altered levels of miR-31: overexpression was obtained through infection with a lentivirus construct carrying the pri-miR-31 sequence under the strong and constitutive U1snRNA promoter (LmiR-31), while depletion was obtained via administration of specific anti-miR-31 LNA oligos (LNA-31). When cells were induced to differentiate, a consistent decrease of dystrophin (more than 2-fold) was observed in the presence of persistent expression of miR-31 at 3 days (FIG. 2B); on the contrary, increase in dystrophin levels was detected when cells were treated with anti-miR-31 LNAs along 3 days of differentiation (FIG. 2C). The limited increase (40%) of dystrophin synthesis when cells are treated with anti-miR-31 LNA is probably due to the fact that at that stage of differentiation miR-31 levels start to decrease (FIG. 2A). No effects were observed with a plasmid expressing an unrelated miRNA (lanes ctrl) or with scrambled LNA oligos (lane scramble).

Figure 3:
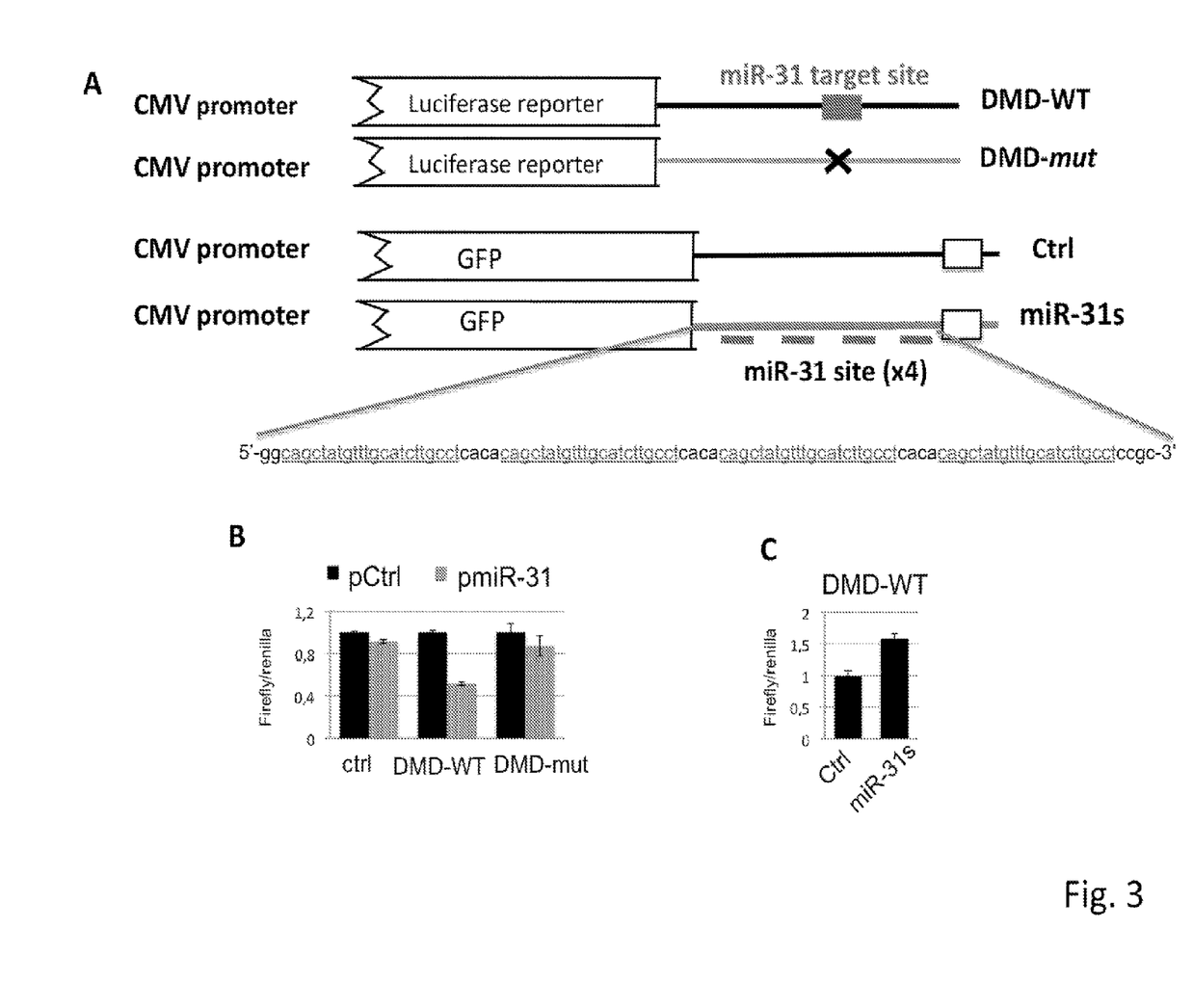
FIG. 3. Dystrophin is target of miR-31. (A) Schematic representation of the constructs utilized: DMD-WT and DMD-mut contain dystrophin wild type 3'UTR or its derivative mutant for the miR-31 target site respectively. Constructs miR-31s and Ctrl contain a 3'UTR with and without 4 miR-31 target sites respectively. (B) C2 myoblasts were transfected with either a control luciferase (Ctrl) or DMD-WT and DMD-mut constructs. Transfections of luciferase reporter plasmids were performed with a vector expressing miR-31 (pmiR-31) or with a control plasmid (pCtrl); luciferase activity measured after 24 h. (C) Luciferase activity of the DMD-WT was measured in C2 myoblasts 24 h after co-transfection with miR-31s or with a control vector.

Dystrophin mRNA was validated as a miR-31 target through the classical luciferase assay: wild type and mutated derivatives of the dystrophin 3'UTR were fused to the luciferase reporter ORF (FIG. 3A) and enzyme activity was measured in conditions of miR-31 overexpression (FIG. 3B). The results indicate that miR-31 represses luciferase activity only in the presence of a dystrophin wild type 3'UTR (DMD-WT). When the same cells were treated with a Sponge construct (Gentner et al., 2009; Brown and Naldini, 2009) containing multiple sites for miR-31 (FIG. 3A, miR-31s), a partial recovery of luciferase activity was obtained (FIG. 3C).

Figure 4:
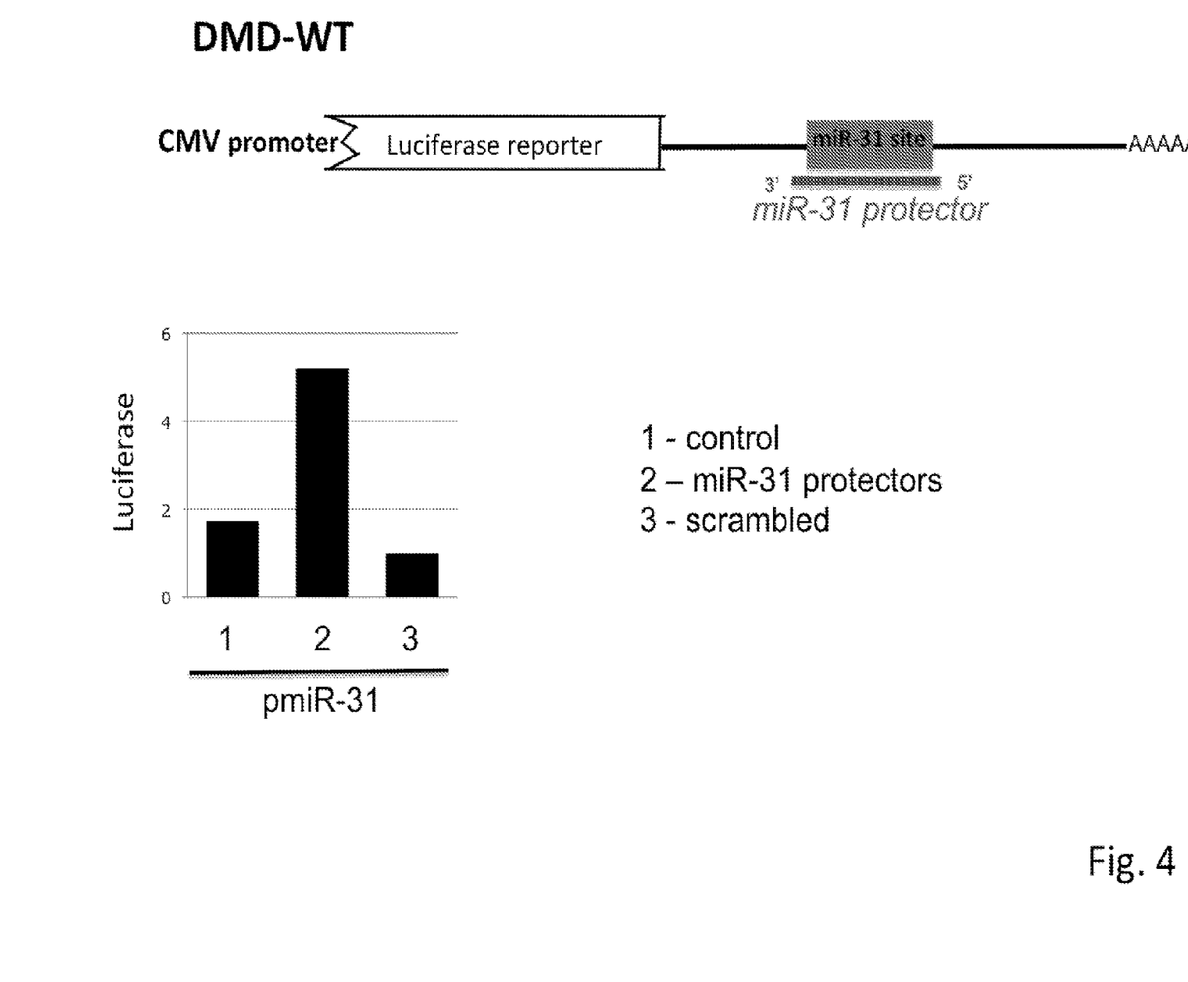
FIG. 4. Dystrophin miR-31 target protection. The DMD-WT construct was transfected in proliferating C2 myoblasts in combination with the pmiR-31 plasmid (bar#1, 2 and 3). Subsequently, LNA oligos complementary to the miR-31 site were transfected (bar#2) in parallel with control scrambled oligos sequence (bar#3). Luciferase activity was measured 36 hours after transfection.

An alternative way to prevent miR-31 repression was obtained through the use of an "oligo protector" ("miR-31 protector"); this oligo contains sequences complementary to the miR-31 target site present on the dystrophin 3'UTR. C2 myoblasts were transfected with the construct containing the dystrophin 3'UTR fused to the luciferase ORF (DMD-WT) together with a plasmid overexpressing miR-31. Under these conditions, the luciferase activity is strongly inhibited due to the repressing activity of miR-31. When a LNA oligonucleotide complementary to the recognition site of miR-31 was co-transfected, luciferase activity was strongly increased (FIG. 4, bar#2). As control, no treatments (bar#1) or scrambled LNA oligos treatments (bar#3), were not able to interfere with miR-31 repressing activity.

Figure 5:
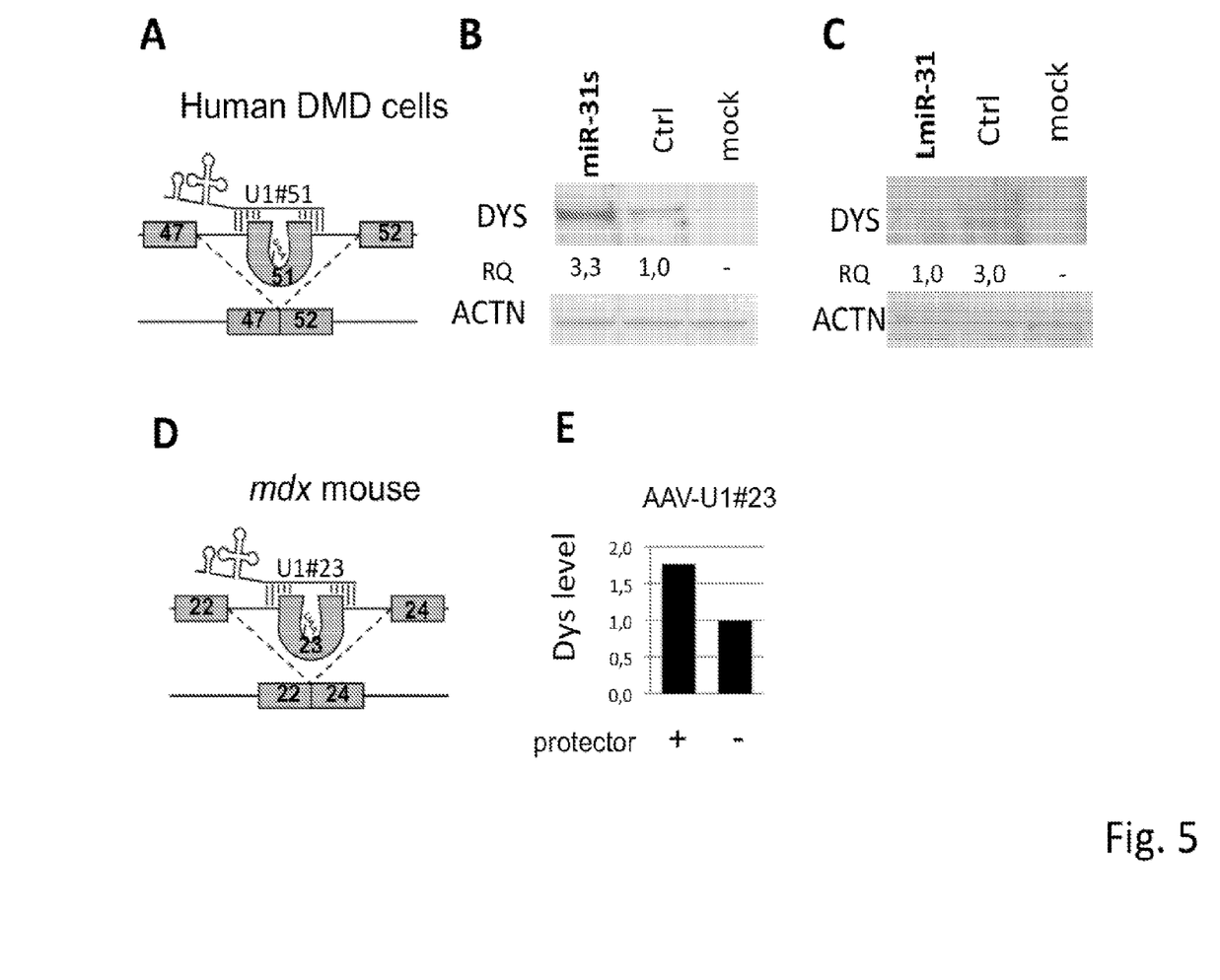

One of the most utilized approaches for the DMD gene therapy is exon skipping (FIG. 5A). This methodology makes use of antisense molecules able to induce the exclusion, during the splicing reaction, of specific dystrophin mutated exons, producing a shorter but functional RNA (De Angelis et al., 2002, Aartsma-Rus et al., 2009). As a consequence of this treatment, dystrophin rescue can be obtained with consequent partial recovery of the pathogenic traits and rescue of morpho-functional parameters (Goyenvalle et al., 2004, Denti et al., 2006 and 2008, Aartsma-Rus et al., 2009). DMD myoblasts deriving from a patient with deletion of dystrophin exons 48-50 were infected with a lentiviral construct expressing an antisense RNA able to induce skipping of exon 51 (lenti-U1#51). Exclusion of this exon from the mature mRNA is able to rescue the open reading frame of the transcript and to induce the production of a shorter but functional dystrophin (De Angelis et al., 2002). However, through this strategy, the levels of dystrophin are rescued at maximum 10-20% of wild type levels. In order to check whether dystrophin synthesis could be further improved by reducing miR-31 levels, we tested the ability of the miR-31s construct, containing 4 binding sites for miR-31, to increase dystrophin levels when infected in Δ48-50 DMD myoblasts. The sponge construct was indeed able to increase by 40% the synthesis of dystrophin when exon skipping was applied to these cells (FIG. 5B, lane miR-31s). In line with this, the overexpression of miR-31 produced a decrease in dystrophin accumulation (FIG. 5C).

In order to study the beneficial effect of preventing miR-31 repression in vivo, we took advantage of the mdx mouse in which dystrophin rescue can be obtained through the skipping of exon 23 (Denti et al., 2006). AAV viruses, expressing exon 23-antisense RNAs (AAV-U1#23, FIG. 5D), were injected into tibialis muscles. After one week, miR-31 target protector LNA oligos were locally injected in the right tibialis, while control scrambled oligos were administered in the contro-lateral leg. After an additional week, muscles were dissected and proteins analyzed. FIG. 5E shows that the miR-31 protector oligos induce doubling of dystrophin synthesis. The indicated values are the average of multiple independent experiments.

Altogether, our data show that dystrophin is targeted by miR-31. In physiological conditions the decrease of miR-31 during differentiation accompanies the increase of the terminal differentiation marker dystrophin; in dystrophic muscles, due to reduced terminal differentiation and intensive regeneration due to activated satellite cells, miR-31 levels remain at high levels. Since the contribution to dystrophin production by regenerating fibers in a compromised muscle is quite relevant, miR-31 repression in this compartment can represent a way for increasing dystrophin translation. Rescue of consistent levels of dystrophin will also have additional benefits such as the completion of the maturation process.

Therefore, the possibility of artificially decreasing miR-31 (through a muscle-specific expression of sponge constructs) or preventing its ability to bind the dystrophin 3'UTR (through protector oligos) represent good improvements to the exon skipping approach or other strategies where one wants to increase the efficiency of dystrophin translation in the treatment of Duchenne Muscular Dystrophy.

REFERENCES

Aartsma-Rus, A., Fokkema, I., Verschuuren, J., Ginjaar, I., van Deutekom, J., van Ommen, G. J., den Dunnen, J. T. (2009). Theoretic applicability of antisense-mediated exon skipping for Duchenne muscular dystrophy mutations. *Hum Mutat.* 30, 293-299.

Bonci, D, Cittadini, A, Latronico, M V, Borello, U, Aycock, J K, Drusco, A et al. (2003). 'Advanced' generation lentiviruses as efficient vectors for cardiomyocyte gene transduction in vitro and in vivo. *Gene Ther.* 10(8): 630-6.

Brown B D, Naldini L. (2009) Exploiting and antagonizing microRNA regulation for therapeutic and experimental applications. *Nat Rev Genet.* 10:578-85.

Buckingham M, Relaix F. (2007) The role of Pax genes in the development of tissues and organs: Pax3 and Pax7 regulate muscle progenitor cell functions. *Annu Rev Cell Dev Biol.* 23:645-73.

Chen J. F. et al. (2006) The role of microRNA-1 and microRNA-133 in skeletal muscle proliferation and differentiation. *Nat Genet.* 38:228-33.

De Angelis, F. G., Sthandier O., Berarducci, B., Toso, S., Galluzzi, G., Ricci, E., Cossu, G., Bozzoni, I. (2002). Chimeric snRNA molecules carrying antisense sequences against the splice junctions of exon 51 of the dystrophin pre-mRNA induce exon skipping and restoration of a corrected phenotype in D48-50 DMD cells. *Proc. Natl. Acad. Sci.* 99, 9456-9461.

Denti, M. A., et al. Body-wide gene therapy of Duchenne Muscular Dystrophy in the mdx mouse model. *Proc. Natl. Acad. Sci. USA* 103:3758-3763 (2006).

Denti M. A., et al. Life-long benefit of AAV/antisense-mediated exon skipping in dystrophic mice. *Hum. Gene Ther.* 19:601-608 (2008).

Eisenberg, I., et al. Distinctive patterns of microRNA expression in primary muscular disorders. *Proc. Natl. Acad. Sci. USA* 104:17016-17021 (2007).

Ervasti, J. M., Sonnemann, K. J. Biology of the striated muscle dystrophin-glycoprotein complex. *Int Rev Cytol.* 265:191-225 (2008).

Gentner B, Schira G, Giustacchini A, Amendola M, Brown B D, Ponzoni M, Naldini L. (2009) Stable knockdown of microRNA in vivo by lentiviral vectors. *Nat Methods.* 6:63-6.

Goyenvalle A, Vulin A, Fougerousse F, Leturcq F, Kaplan J C, Garcia L, Danos O. (2004) Rescue of dystrophic muscle through U7 snRNA-mediated exon skipping. *Science.* 306: 1796-9.

Matsumura, K., et al. Expression of dystrophin-associated proteins in dystrophin-positive muscle fibers (revertants) in Duchenne muscular dystrophy. *Neuromuscul. Disord.* 4:115-120 (1994).

Naguibneva I. et al. (2006) The microRNA miR-181 targets the homeobox protein Hox-A11 during mammalian myoblast differentiation. *Nat Cell Biol.* 8 :278-84.

Pena J T, Sohn-Lee C, Rouhanifard S H, Ludwig J, Hafner M, Mihailovic A, Lim C, Holoch D, Berninger P, Zavolan M, Tuschl T. (2009) miRNA in situ hybridization in formaldehyde and EDC-fixed tissues. *Nat Methods.* 6:139-41.

Rivas F V, Tolia N H, Song J J, Aragon J P, Liu J, Hannon G J, Joshua-Tor L. (2005) Purified Argonaute2 and an siRNA form recombinant human RISC. *Nat Struct Mol Biol.* 12(4):340-9.

The invention claimed is:

1. A nucleic acid molecule or a derivative thereof wherein the derivative is a DNA molecule coding the nucleic acid molecule and wherein the nucleic acid molecule is:

5'ggcagcuauguuugcaucuugccucaca-
cagcuauguuugcaucuugccucaca-
cagcuauguuugcaucuugccucaca cagcuauguuugcaucu-
ugccuccgc-3'(SEQ ID NO: 4), 5'-gaaauggcaaguuau-3' (SEQ ID NO: 1) or 5'-ccauauaaagaaauggcaaguua-3' (SEQ ID NO: 2).

2. The nucleic acid molecule or a derivative thereof according to claim 1 located within the 3'UTR of a transcript whose expression is driven by a muscle-specific promoter.

3. The nucleic acid molecule or a derivative thereof according to claim 1, being a modified synthetic oligonucleotide.

4. The nucleic acid molecule or a derivative thereof according to claim 3 wherein the modified synthetic oligonucleotide is selected from the group consisting of: LNA (Locked Nucleic Acid), methylated oligos, and phosphoro-thiolated oligos.

5. An expression vector for gene therapy comprising a sequence encoding the nucleic acid molecule according to claim 1 and a muscle-specific promoter operatively linked to the sequence.

6. The expression vector for gene therapy according to claim 5 being an AAV derived vector.

7. A method for increasing the translation of dystrophin in a host in need thereof, which method comprises administering to the host a therapeutically active amount of a nucleic acid molecule, or a derivative thereof, wherein the derivative is a DNA molecule coding the nucleic acid molecule, or an expression vector comprising the derivative, wherein the nucleic acid molecule is:

5'ggcagcuauguuugcaucuugccucaca-
cagcuauguuugacucuugccucaca-
cagcuauguuugcaucuugccucaca cagcuauguuugcaucu-
ugccuccgc-3'(SEQ ID NO: 4), 5'-gaaauggcaaguuau-3' (SEQ ID NO: 1) or 5'-ccauauaaagaaauggcaaguua-3' (SEQ ID NO: 2).

8. The method according to claim 7, wherein the expression vector comprises a muscle-specific promoter operatively linked to the nucleic acid molecule.

9. A method of treating muscle degenerative disorders comprising administering to the host a therapeutically active amount of a nucleic acid molecule, or a derivative thereof, wherein the derivative is a DNA molecule coding said nucleic acid molecule, or an expression vector comprising the derivative, wherein the nucleic acid molecule is:

5'ggcagcuauguuugcaucuugccucaca-
cagcuauguuugcaucuugccucaca-
caguauguuugaucuucgccucaca cagcuauguuugacaucu-
ugccuccgc-3'(SEQ ID NO: 4), 5'-gaaauggcaaguuau-3' (SEQ ID NO: 1) or 5'-ccauauaaagaaauggcaaguua-3' (SEQ ID NO: 2).

10. A method according to claim 9 wherein the muscle degenerative disorder is a Muscular Dystrophy.

11. The method according to claim 10 wherein the muscular dystrophy is Duchenne Muscular Dystrophy.

12. The expression vector for gene therapy according to claim 5 being a lentivirus vector.

13. The method according to claim 7 wherein the expression vector is an AAV derived vector.

14. The method according to claim 9 wherein the expression vector is an AAV derived vector.

15. The method according to claim 7 wherein the expression vector is a lentivirus vector.

16. The method according to claim 9 wherein the expression vector is a lentivirus vector.

17. The derivative according to claim 1 being 5'-ggcagctatg tttgcatctt gcctcacaca gctatgtttg catcttgcct cacacagctatgtttg-catc ttgcctcaca cagctatgtt tgcatcttgc ctccgc-3' (SEQ ID NO: 5).

18. The method according to claim 7 wherein the derivative is 5'-ggcagctatg tttgcatctt gcctcacaca gctatgtttg catcttgcct cacacagctatgtttgcatc ttgcctcaca cagctatgtt tgcatcttgc ctccgc-3' (SEQ ID NO: 5).

19. The method according to claim 9 wherein the derivative is 5'-ggcagctatg tttgcatctt gcctcacaca gctatgtttg catcttgcct cacacagctatgtttgcatc ttgcctcaca cagctatgtt tgcatcttgc ctccgc-3' (SEQ ID NO: 5).

20. The method according to claim 7 wherein the nucleic acid molecule or a derivative thereof is a modified synthetic oligonucleotide.

21. The method according to claim 9 wherein the nucleic acid molecule or a derivative thereof is a modified synthetic oligonucleotide.

22. The method according to claim 20 wherein the modified synthetic oligonucleotide is selected from the group consisting of LNA (Locked Nucleic Acid), methylated oligos, and phosphoro-thiolated oligos.

23. The method according to claim 21 wherein the modified synthetic oligonucleotide is selected from the group consisting of LNA (Locked Nucleic Acid), methylated oligos, and phosphoro-thiolated oligos.

\* \* \* \* \*